US00PP18265P3

(12) United States Plant Patent
Korlipara

(10) Patent No.: US PP18,265 P3
(45) Date of Patent: Dec. 4, 2007

(54) ***COREOPSIS* PLANT NAMED 'PINK LEMONADE'**

(50) Latin Name: ***Coreopsis* hybrid**
Varietal Denomination: Pink Lemonade

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 11/343,831

(22) Filed: Jan. 30, 2006

(65) Prior Publication Data

US 2007/0180590 P1 Aug. 2, 2007

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—June Hwu
(74) *Attorney, Agent, or Firm*—Klarquist Sparkman, LLP

(57) ABSTRACT

A new and distinct *Coreopsis* plant named 'Pink Lemonade' characterized by yellow foliage, pink flowers, and a dwarf habit.

1 Drawing Sheet

Botanical denomination: *Coreopsis* hybrid (parents unknown).

Variety designation: 'Pink Lemonade'.

Cross reference to: co-pending applications for *Coreopsis* 'Cherry Lemonade' (U.S. application Ser. No. 11/343,832, filed Jan. 30, 2006) and 'Strawberry Lemonade' (U.S. application Ser. No. 11/344,356 filed Jan. 30, 2006).

BACKGROUND OF THE INVENTION

The present invention relates to a new and distinct plant of *Coreopsis* and given the cultivar name 'Pink Lemonade'. *Coreopsis* is in the family Asteraceae. This new cultivar originated from offspring located at the nursery in Canby, Oreg. and reproduced in tissue culture where further selections were made. This selection was made for its pink flowers.

SUMMARY OF THE INVENTION

The following traits have been repeatedly observed and are determined to be the unique characteristics of 'Pink Lemonade'. These characteristics in combination distinguish 'Pink Lemonade' as a new and distinct cultivar:

1. Unique golden yellow foliage.
2. Pink daisy-type flowers.
3. Dwarf mounding habit.
4. Very free flowering.

This new cultivar has been reproduced only by asexual propagation (division and tissue culture). Each of the progeny exhibits identical characteristics to the original plant. Asexual propagation by cuttings and tissue culture using standard micropropagation techniques with terminal and lateral shoots, as done in Canby, Oreg. shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE PHOTOGRAPH

The photograph shows a one year old *Coreopsis* 'Pink Lemonade' growing in the ground in the field in August in Canby, Oreg.

DETAILED PLANT DESCRIPTION

The following is a detailed description of the new *Coreopsis* cultivar based on observations of a one-year-old specimen grown in a container in the greenhouse over the winter and then planted on May 1$^{st}$ in the ground in the trial fields in full sun. The data was taken in August from this material. The trial fields are under typical outdoor conditions in Canby, Oreg. Canby is Zone 8 on the USDA Hardiness map. Temperatures range from a high of 95 degrees F. in August to 32 degrees F. in January. Normal rainfall in Canby is 42.8 inches per year. The color descriptions are all based on The Royal Horticultural Society Colour Chart.

Plant:
- *Type.*—Herbaceous perennial.
- *Hardiness.*—USDA Zones 9 to 10.
- *Size.*—40 cm wide and 25 cm tall to top of flowers.
- *Form.*—Low mound with freely branching stems.
- *Vigor.*—Excellent.
- *Roots.*—Fibrous, freely branching, fine and White 155A in color. Roots develop easily from cuttings.

Stem:
- *Type.*—Ascending.
- *Size.*—20 cm tall and 1 to 2 mm wide.
- *Internode length.*—12 to 30 mm.
- *Surface.*—Glabrous.
- *Color.*—Yellow Green 146C.

Leaf:
- *Type.*—Simple.
- *Shape.*—Linear.

*Arrangement.*—Opposite.
*Length.*—25 to 40 mm, sessile.
*Width.*—1 to 2 mm.
*Margins.*—Entire.
*Apex.*—Acute.
*Base.*—Attenuate.
*Surface texture.*—Soft, smooth, glabrous on both surfaces.
*Venation.*—Pinnate.
*Color.*—Top side — Yellow, Yellow 10A with a green main vein Yellow Green 146C to Yellow green 146A where shaded. Bottom — same as top side.

Inflorescence:
*Type.*—Long stalked terminal heads of daisy type flowers.
*Size.*—2.5 to 3.5 cm wide and 8 mm deep.
*Bud.*—Oval in shape, 3.5 mm long and 3 mm wide, glabrous, Green 148A on the bottom half, Greyed Yellow 161A on top half with Greyed Red 178A at the tip and in the seams.
*Peduncle.*—7 cm tall and 1 mm wide, glabrous, Yellow 10A to Yellow Green 146C where shaded.
*Ray florets.*—No pistil or stamen. Number — 8. Shape: Obovate with the tip three lobed, with lobes obtuse and the central lobe the longest, base attenuate, margins entire. Size: Grows to 17 mm long, 8 mm wide. Surface texture: Soft, velvety, both sides glabrous. Color: Ray floret, topside — Red Purple 70 A to Purple 79A overall. Ray, bottom side — Purple 77C.
*Disc.*—Shape: Conic, deeper with maturity. Size: 7 mm wide and becoming 5 mm deep with maturity. Color: Brown 200B when in bud, opening to orange, Orange 24A with a dark background, Greyed Purple 187A.
*Disc florets.*—About 45 in number, 5 mm long and 1 mm wide, tubular, 4 lobed, Greyed Purple 187A at the apex to Orange 24A in middle and Yellow Orange 20B near base. Pistil — 1 in number, 6 mm long, Orange 24A overall, extruding, 2-branched stigma, ovary 1.5 mm long, style 4 mm long. Stamen — 4, filaments 3 mm long, extruding, Black 202A. Pollen color — Yellow 12C.
*Phyllaries.*—In two series, inner series opaque, 8 in number, rotate, Green 148A on the bottom half, Greyed Orange 164B on top half, each 4 mm long and 1.5 mm wide, ovate lanceolate, acute, entire, glabrous; outer series leafy, usually 5 in number, campanulate, each lobe 1.5 mm long and 1 mm wide, Yellow Green 147A with clear margins, ovate, entire, acute, glabrous.
*Receptacle.*—Green 147A, conic, 2 mm long, and 2 mm wide, glabrous.
*Bloom period.*—May through September in Canby, Oreg.
*Fragrance.*—Light, daisy-like.
*Lastingness.*—Each bloom lasts about five days.

Seed: None produced.
*Fertility.*—Infertile.

Disease and pests: *Coreopsis* are susceptible to mildew and fungal spots. None of these have been observed on plants grown under commercial conditions in Canby, Oreg.

COMPARISONS TO SIMILAR *COREOPSIS*

Compared to *Coreopsis* 'Limerock Ruby' (U.S. Plant patent application Ser. No. 20030066114), this new cultivar has the same flower size but has a much shorter habit, yellow foliage rather than green, and pink rather than rose pink flowers.

I claim:

1. A new and distinct *Coreopsis* plant named 'Pink Lemonade' as herein illustrated and described.

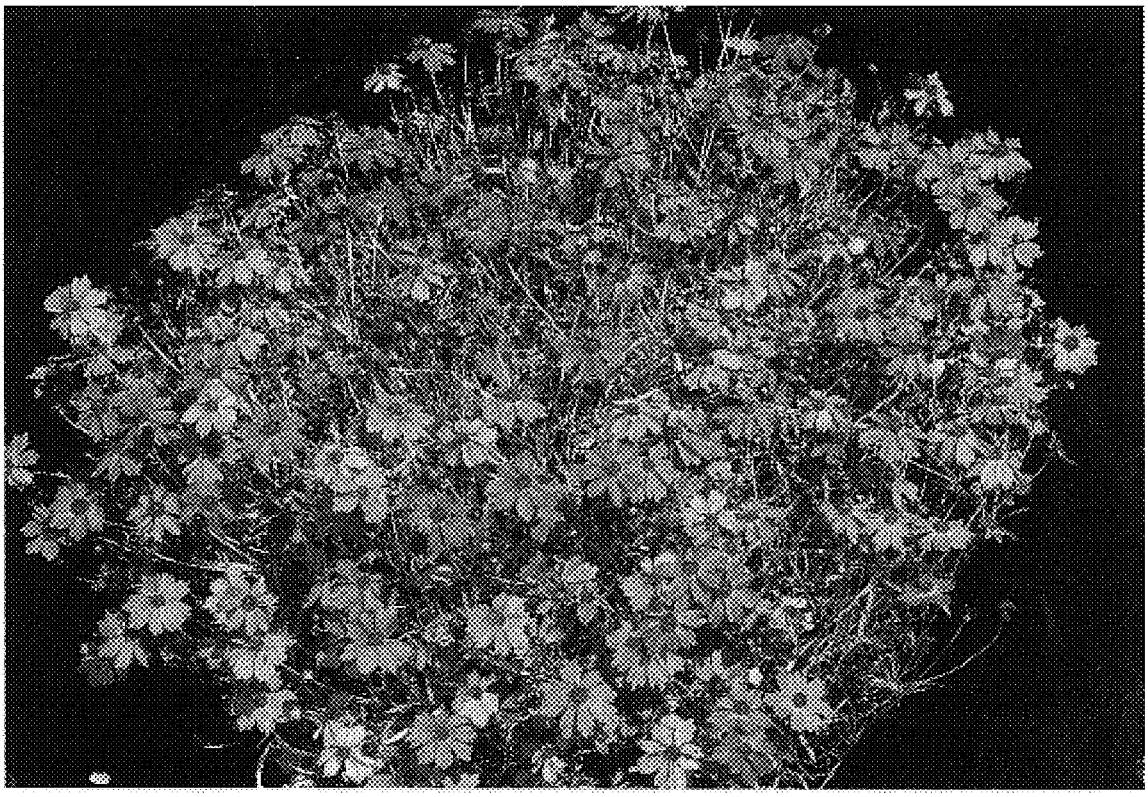

* * * * *